(12) United States Patent
Van Oort et al.

(10) Patent No.: US 6,245,339 B1
(45) Date of Patent: Jun. 12, 2001

(54) MEDICAMENT CARRIER WITH AGGLOMERATED LARGE MEDICAMENT PARTICLES AND RELATED METHOD OF MANUFACTURE THEREOF

(75) Inventors: Michiel Mary Van Oort, Durham; Mark Joseph Sacchetti, Raleigh, both of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/230,613

(22) PCT Filed: Jul. 30, 1997

(86) PCT No.: PCT/EP97/04128

§ 371 Date: Jan. 28, 1999

§ 102(e) Date: Jan. 28, 1999

(87) PCT Pub. No.: WO98/04308

PCT Pub. Date: Feb. 5, 1998

(30) Foreign Application Priority Data

Jul. 31, 1996 (GB) .................................................. 9616047

(51) Int. Cl.[7] ............................. A61K 9/00; A61M 15/00; A61M 16/10; A61M 16/00
(52) U.S. Cl. ............... 424/400; 128/203.12; 128/203.13; 128/203.15; 128/203.19; 128/203.21; 128/203.23
(58) Field of Search ........................ 424/400; 128/203.12, 128/203.13, 203.15, 203.19, 203.21, 203.23

(56) References Cited

U.S. PATENT DOCUMENTS

| | | | |
|---|---|---|---|
| 5,503,869 | * | 4/1996 | Van Oort .......................... 427/2.14 |
| 5,647,347 | * | 7/1997 | Van Oort ........................ 128/203.15 |
| 5,823,182 | * | 10/1998 | Van Oort ........................ 128/203.12 |

FOREIGN PATENT DOCUMENTS

| | | |
|---|---|---|
| 92 00115 | 1/1992 | (WO) . |
| 96 12515 | 5/1996 | (WO) . |
| 96 40068 | 12/1996 | (WO) . |

* cited by examiner

Primary Examiner—Thurman K. Page
Assistant Examiner—Todd D. Ware
(74) Attorney, Agent, or Firm—James P. Riek

(57) ABSTRACT

A medicament carrier (10) having a first and a second spaced apart screen (12, 14) each of which has surfaces (12B, 14B) defining a plurality of interstices (12A, 14A). The carrier (10) contains powdered agglomerated medicament particles (SM) loaded onto the first screen surface (12B) such that the interstices (12A) of the first screen (12) are at least partially open and free of the agglomerated medicament particles (SM). When an air stream is provided to the carrier to entrain the agglomerated powdered medicament particles (SM) and move them from the first screen (12) through the interstices (14A) of the second screen (14), the agglomerated powdered medicament particles (SM) are sheared by air flow gradients created by the first and second screens (12, 14) and by contact with the surface (14B) of the second screen (14) to create particles of respirable particle size range. The carrier (10) can be used in a dry powder inhalator device.

35 Claims, 5 Drawing Sheets

DISPERSED DRUG

SSP

SM 14
14A
12
12A

AF

BREATH → AIR BLAST

040 RPM

MEDICAMENT CARRIER WITH AGGLOMERATED LARGE MEDICAMENT PARTICLES AND RELATED METHOD OF MANUFACTURE THEREOF

The present invention relates, in general, to a medicament carrier containing particulate dry powder medicament and which is adapted to be positioned within a dry powder inhalator. More particularly, the present invention relates to a medicament carrier containing agglomerated dry powder medicament particles having a particle size of about 0.05 millimeter or greater.

Asthma and other respiratory diseases are typically treated by the inhalation of an appropriate medicament for deposition into the lungs to ease patient breathing and increase air capacity. The most widely used treatments for respiratory diseases have been (1) the inhalation of a medicament from a drug solution or suspension in a metered dose aerosol container (i.e., a pressurized inhalator) using a gas propellant and (2) the inhalation of a powdered drug (generally admixed with an excipient) from a dry powder inhalator.

However, in view of recent evidence of the link between chlorofluorocarbon gas emissions and the deterioration of the earth's protective ozone layer, use of drugs in pressurized aerosol inhalators using chlorofluorocarbons as the gas propellant is less desirable and interest in dry powder inhalation systems has substantially increased.

Applicants are presently aware of several different dry powder methods and devices for providing fine particulate powders to the respiratory tract of a patient. The dose of a powder type of medicament employed with such dry powder inhalator devices is, in most instances, significantly less than 50 mg, typically less than 5 mg, and usually about 50 to about 500 micrograms. The powdered particles contained in the inhalator are micronized, typically having a particle size of <10 micrometers, more particularly <6 micrometers, even more particularly <5 micrometers, which is an appropriate size so that the particles can be drawn deep into the lungs.

One such inhalator device utilizes hard gelatin capsules which contain a dose of the powdered medicament and possibly also various adjuvants. The inhalator includes a mechanism for perforating the capsule in order to open it after it has been inserted into the inhalator. An air stream generated by the patient on the mouthpiece of the inhalator removes and disaggregates the powder contained within the capsule which is inhaled by the patient. The empty capsule is then expelled from the inhalator, so that it may receive the next capsule. A drawback of this device is that the air stream created by the patient is generally not sufficient in duration and velocity to remove, disaggregate and aerosolize all of the powder from the capsule. Dry powder inhalators using this technology are disclosed in a number of patents including U.S. Pat. Nos. 3,906,950; 4,013,075; 3,807,400; and 3,991,761, all to Cocozza.

Also related to the above-mentioned capsule technology are the disclosures of U.S. Pat. No. 4,161,516 to Bell and U.S. Pat. No. 4,395,421 to Taylor et al. These patents show, respectively, an agglomerator-pelletizer apparatus and a wet granulator apparatus for preparing pellets or granules of the asthma medicament, disodium cromoglycate, which may then be placed inside of a capsule.

Another type of inhalator device is loaded with a package having a number of spaced-apart blisters, each containing powdered medicament for administration to the patient. As the patient moves each blister into a predetermined position, the patient breaks the blister by a mechanism in the device so as to release the powder and inhale it. However, moisture ingress into the blister package can cause aggregation into large agglomerates of the prepared medicament therein. Consequently, when the prepared medicament is inhaled by the patient, the preferred particle size for greatest efficacy in respiratory disease treatment may not necessarily be achieved. Instead, like the gelatin capsules previously discussed, the airstream created by the patient is not sufficient in duration and velocity to remove, disaggregate and aerosolize all of the powder from the blister to the desired particle size. This type of inhalation device is disclosed in a number of published patent applications including European Published Patent Application Nos. 0 455 463 A1 to Velasquez et al., 0 211 595 A2 to Newell et al., and 0 4670 172 A1 to Cocozza et al.

Yet another type of dry powder inhalator contains a quantity of powdered medicament therein which is sufficient for multiple doses. A representative example of this type of device is the TURBUHALER® inhalator which is disclosed in U.S. Pat. Nos. 4,668,218; 4,667,668; and 4,805,811. The inhalator includes a mechanism for withdrawing powdered medicament from a container therein and for preparing a dose for inhalation, including a plate having a number of cup-shaped holes therethrough. The plate can be moved by mechanical means from a position where a proportion of the holes are filled with powdered medicament taken from the container to another position in which the holes filled with the medicament are located within a channel. Air flows into the channel as a result of suction provided by the patient on a mouthpiece in communication with the channel so as to remove the powdered medicament from the holes. Several undesirable consequences are associated with this system. It has been found that when suction is applied to entrain the medicament from one or more holes in the plate, not all of the medicament is entrained in the air flow. Further, particle size distribution is strongly dependent on the inhalation profile of the patient, which is a disadvantage with patients suffering from acute respiratory problems. Moreover, the TURBUHALER® device is designed to administer large doses and is prone to significant variations in medicament delivery. Lastly, the powder must travel a lengthy path resulting in significant losses due to wall deposits.

A fourth dry powder inhalator device is disclosed in PCT Published Application No. WO 92/00115, published Jan. 9, 1992, to Gupte et al., which shows a velour-type or velvet-type fiber material loaded with powder between the fibers. An air stream acts to lift the powder from the velour-like carrier material and to entrain the powder within the air stream which is then inhaled by the patient. One potential shortcoming of this type of inhalator device is that there can be a tendency for the carrier fibers of velour or velvet to dislodge and to intermix with the medicament ultimately being deposited within the patient's lungs. In loading the velour or velvet carrier, powder is coated thereon and then pressed and scraped with a blade to press the powder between the fibers and disagglomerate large clumps of the powder. Alternatively, the powder may be loaded between the fibers from droplets of a suspension of the powder and a suspending agent (such as dichloromethane) dispersed from a metering device.

A new type of carrier disc for use with a dry powder inhalator is described in PCT Published Application No. WO 94/20164, published Sep. 15, 1994, to Mulhauser et al. The carrier disc is a screen mesh which is impregnated in spaced locations or interstices along its circumference with a dose of powdered asthma medicament, such as salmeterol hydroxynapthoate. During inhalation, air impinging on the powdered medicament impregnated into the interstices of the screen surrounds each medicament dose and entrains it to dispense it from the screen interstices into the air-stream and in turn into the patient's lungs. Shortcomings of the interstitial deposit of the powdered medicament into the screen (i.e., impregnation of the medicament in the screen interstices) are limitations of dose size to interstitial volume, and the necessity to disaggregate large clusters of medicament present in interstitial voids.

An improvement over the carrier screen disclosed in the above-mentioned PCT Published Application No. WO 94/20164 is described in U.S. patent application Ser. Nos. 08/328,577 and 08/328,578, both to Van Oort and both filed on Oct. 21, 1994, the disclosures of which are incorporated herein by reference. These two applications describe a medicament carrier which is adapted for use in a dry powder inhalator device and includes at least one carrier screen having carrier surfaces defining a plurality of interstices in the screen and loaded with at least one dose of a powdered medicament such that the powdered medicament is loaded onto the carrier screen surfaces whereby the interstices of the screen are at least partially open and free of the powdered medicament. Thus, much greater flexibility in medicament dose range is provided with a specific carrier screen interstice size since the medicament dose is not impregnated into the interstices and thus is not dependent on the interstitial void volume of the carrier screen. For loading the dose of powder onto the screen for the dosing thereof via an inhalator, a selected amount of the powder (such as 50 micrograms) is admixed with a suspending agent (such as perfluoropentane) and then the resultant suspension is dropped onto the screen after which the suspending agent evaporates and leaves micronized dry powder particles on the screen surfaces.

In accordance with the present invention, there is provided a medicament carrier for use in an inhalator device, the medicament carrier comprising a first screen having a surface defining a plurality of interstices therein, wherein the first screen is loaded with one or more doses of dry powdered agglomerated medicament particles wherein the agglomerated medicament particles are loaded onto the surface of the first screen such that the interstices thereof are at least partially open and free of the agglomerated medicament particles and such that the first screen serves as a carrier screen for the agglomerated medicament particles; and a second screen spaced apart from the first screen, and the second screen having a surface defining a plurality of interstices therein.

The first screen serves as a carrier screen for a powdered medicament and the second screen serves as an impaction and shearing screen for the powdered medicament. The two screens together serve to contain the medicament.

Particularly, the interstices of the first screen may be smaller than or equal to the interstices of the second screen.

Upon the surface of the first screen, at least one dose of a powdered medicament is loaded, whereby the interstices of the first screen are at least partially open and free of the powdered medicament. The powdered medicament loaded upon the surface of the first screen comprises agglomerated particles, typically having a particle size from about 0.05 millimeters to about 3.0 millimeters.

When the powdered agglomerated medicament particles are removed by an air flow entering through the interstices of the first screen and are dislodged, entrained, and/or disaggregated by the air flow therethrough, then, (i) the first screen serves to present the powdered medicament to the air stream or air flow path and will act as a source of multiple air jets on the powdered agglomerated medicament particles and (ii) the second screen will shear the powdered agglomerated medicament particles and further disaggregate them due to impaction and high shear forces resulting from contact of the powdered agglomerated medicament particles with the surface of the second screen as they pass through the interstices of the second screen and are dispersed into smaller particles within a desirable respirable particle size range.

Furthermore, the present invention provides a process for dispersing the agglomerated medicament particles from the carrier as described in the two paragraphs above. The process comprises providing an air stream or air flow to the carrier to entrain and disaggregate the agglomerated powdered medicament particles and move them from the first carrier screen, which acts as a source of multiple air jets on the powdered agglomerated medicament particles, through the interstices of the second carrier screen whereby the agglomerated powdered medicament particles are further sheared by the surface of the second carrier screen into smaller particles of a desirable respirable particle size range. Particularly, the particles of the desirable respirable particle size range should have a mass median aerodynamic diameter from about 0.5 micrometers to about 6.0 micrometers, more particularly from about 1 micrometers to about 4.5 micrometers. Also particularly, the particles of the desirable respirable particle size range should have more than 50% thereof, more particularly more than 70% thereof, and even more particularly close to 100% thereof with a mass median aerodynamic diameter <10 micrometers, more particularly <6 micrometers, and even more preferably <5 micrometers.

Additionally, the present invention provides a process for forming a medicament carrier to use in a dry powder inhalator device. The process comprises providing a powdered medicament such that the powdered medicament comprises agglomerated particles, typically having a size from about 0.05 millimeters to about 3.0 millimeters. Further, the process comprises providing a medicament carrier which includes at least a first screen and a second screen spaced therefrom, each screen having a respective surface defining a plurality of interstices therebetween. Particularly, the interstices of the first screen may be smaller than or equal to the interstices of the second screen, but could also be larger. The first screen serves as a carrier screen for the agglomerated powdered medicament particles. Also, when an air stream or air flow is presented to the carrier, the first screen serves to present the powdered medicament to the air stream or air flow path and will act as a source of multiple air jets or forces on the powdered agglomerated medicament particles. The second screen serves as an impaction and shearing screen for the agglomerated powdered medicament particles. The process additionally comprises applying at least one dose of the agglomerated powdered medicament particles to the carrier surface of the first screen such that the agglomerated powdered medicament particles are loaded upon the first screen whereby the interstices thereof are at least partially open and free of the powdered medicament.

It is therefore the object of the present invention to provide a medicament carrier for use in a dry powder inhalator which provides for administration of a dosage of powdered medicament wherein the particle size of the particles that leave the inhalator and are inhaled into the patient's lungs are formed in a desirable particle size for maximum beneficial efficiency, providing maximum efficacy to the patient.

It is an advantage of the present invention that, unlike with prior art devices, the medicament need not first be admixed with a liquid suspending agent for application to the carrier.

It is a further advantage of the present invention, unlike prior art devices which result in the patient inhaling medicament particles which are too large, that instead medicament particles are in an appropriate respirable particle size range to be inhaled by the patient.

Some of the objects and advantages of the invention being stated, other objects will become evident as the description proceeds, when taken in connection with the accompanying drawings and Laboratory Examples described hereinbelow.

FIG. 5 is a schematic view of the individual medicament carrier shown in FIG. 4 and illustrating the effect upon the particles in the medicament carrier when subjected to an air pulse;

FIG. 6 is a schematic view of a tumbler/agglomeration device useful in forming agglomerated medicament powder particles in accordance with the present invention;

FIG. 7 is a photomicrograph of tumble-agglomerated medicament powder particles of the medicament, beclomethasone dipropionate; and FIG. 8 is a photomicrograph of tumble-agglomerated medicament powder particles of the medicament, salmeterol hydroxynapthoate, and also of micronized powder particles in the same field of view to demonstrate the difference in particle size.

Referring now to FIGS. 1–5 of the drawings wherein like numerals indicate like elements throughout the several views, 3 embodiments of medicament carrier cassettes or holders are illustrated in FIGS. 1–3, each of which includes a number of spaced-apart medicament carriers 10 therein which form the subject of the instant invention. A plurality of medicament carriers 10 are shown positioned on the perimeter of a medicament carrier cassette such as the rings shown in FIGS. 1 and 2, respectively, or along the length of a medicament carrier cassette tape such as that shown in FIG. 3. After inhalation by the patient through the mouthpiece of an inhalator (not shown), medicament carriers 10 within medicament carrier cassettes such as shown in FIGS. 1–3 are selectively indexed, by suitable mechanical, electromechanical, or other means, to present a new dose of a powdered medicament to the air flow or air pulse of the inhalator device.

It should be appreciated that medicament carrier cassettes of FIGS. 1–3 are configured so as to be insertable into any suitable breath-activated dry powder inhalator (not shown) such as are well known in the art. Moreover, novel medicament carriers 10 of the present invention could be incorporated into many other types of sheets, plates, cylinders, discs and the like in addition to the 3 depicted representative cassettes, which could have an air assist or various other means of activation, including breath-activation.

Referring more specifically to the drawings, medicament carrier 10 is shown in FIGS. 4A and 5. Medicament carrier

10, a plurality of which are included in each of representative medicament carrier embodiments of FIGS. 1–3, is formed from first screen 12 which most suitably is spaced apart from and secured to second screen 14. As shown in FIG. 4B, optional medicament carrier 15 may have an optional third screen 16 with interstices 16A and surface 16B, of the same materials and sizes as described below vis-a-vis first screen 12 and second screen 14. More particularly, screen 16 may be included in carrier 15 and spaced apart from one of first screen 12 or second screen 14. In other words, the third screen may be placed on the side of first screen 12 opposite of the side where second screen 14 is placed, or on the side of second screen 14 opposite of the side where first screen 12 is placed, to facilitate as described below dispersing of agglomerated particles SM into small sheared particles SSP by air flow AF. Particularly, first screen 12 should be spaced from second screen 14 by about 0.002 to about 0.12 inch (about 0.05 to about 3.0 millimeters), more particularly about 0.02 inch (about .51 mm). First screen 12 serves as a carrier screen, whereas second screen 14 serves as a shearing screen, as further described below.

Various materials are suitable for use as screens 12, 14. Physico-chemical properties of the screen material which are important include moisture content, abrasion/heat/chemical resistance, dimensional stability, physical size properties of the screen (such as percent open area for air permeability and such as thread diameter thickness), and weave type.

Regardless of the material used for screens 12, 14, each is always in the form of a mesh (i.e., net-like or grid-like) so as to provide, respectively, a plurality of interstices 12A, 14A and surfaces 12B, 14B (see FIG. 4). Thus, the screen material specifically does not include the velour-type or velvet-type material as is disclosed in the above-mentioned PCT Published Application No. WO 92/00115, published Jan. 9, 1992, to Gupte et al.

Each of screens 12, 14 can be a non-woven or woven screen formed from various materials. For instance, screens 12, 14 may be formed from natural fibers, polymeric synthetic fibers (i.e., materials sold under the trademarks TEFLON® or GORTEX®), metal fibers, or ceramic fibers. The fibers may be surface plasma-treated or may be coated. For instance, polymeric synthetic fibers may be metal coated. Also, screens 12, 14 may be punched or stamped from a blank, such as a metal blank, or can be formed from a photoacid etched material, such as photoacid etched from stainless steel or photoacid etched from ceramic or formed in any other suitable fashion. As a result, provided are a plurality of interstices 12A, 14A in and surfaces 12B, 14B of screens 12, 14, respectively (see FIG. 4). Suitable synthetic polymers include, but are not limited to, nylon, polyester, polypropylene, polyethylene, polytetrafluoroethylene, ethylene-tetrafluoroethylene copolymer (abbreviated herein as ETFE), and ethylene-chlorotrifluoroethylene copolymer (abbreviated herein as E-CTFE). Stainless steel (abbreviated herein as SS) as the metal screen material and non-hygroscopic polymers as the polymeric screen material are particularly useful because moisture is a problem with many dry powder medicament formulations.

Since a polymeric screen material should be relatively non-hygroscopic and hydrophobic, nylon and polyester are less useful than other polymeric screen materials. Polypropylene, ethylene-tetrafluoroethylene copolymer, polytetrafluoroethylene, and polyethylene are all non-hygroscopic and have excellent hydrophobicities and thus are most particularly useful as polymeric screen materials for forming carrier screens 12, 14 of medicament carriers 10 of the invention.

First screen 12 is most suitably formed so as to be about 0.06 to 0.250 inch (about 1.52 to 6.35 mm), more particularly about 0.06 to 0.125 inch (about 1.52 to 3.18 mm), in diameter in size (colloquially referred to as the "dot" size) and to have interstices 12A therein measuring approximately 10 micrometers or more in width, which is a mesh size number of about 1250 or less. It is noted that the larger the interstice width is, then, the smaller the mesh size number is. Surfaces 12B should have a thread thickness from about 0.0005 inch to about 0.004 inch (about 12.7 to about 102 micrometers). Alternatively, screens may be eliptical in configuration.

Like first screen 12, second screen 14 is most suitably formed so as to be about 0.06 to 0.25 inches (about 1.52 to 6.35 millimeters), more particularly about 0.06 to 0.125 inch (about 1.52 to 3.18 mm), in diameter in size and to have interstices 14A therein measuring approximately 10 micrometers or more in width, which is a mesh size of about 1250 or less, and to have surfaces 14B measuring from about 0.0005 inch to about 0.004 inch (about 12.7 to about 102 micrometers) in thread thickness.

Figure 1:
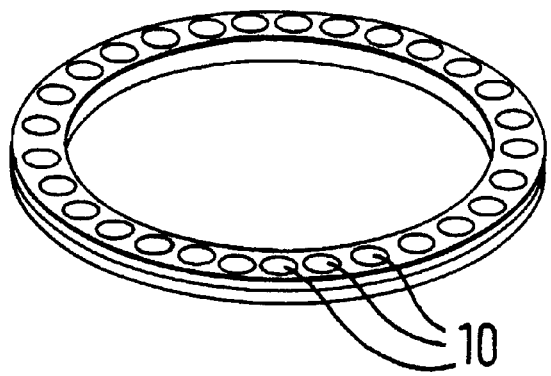
FIG. 1 is a perspective view of a first representative medicament carrier cassette for use in a dry powder inhalator device in accordance with the present invention.
Figure 2:
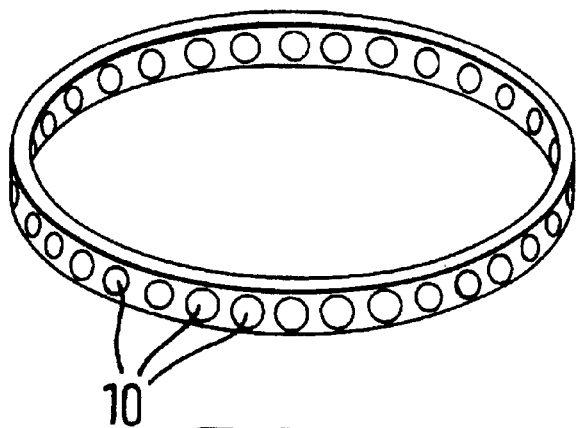
FIG. 2 is a perspective view of a second representative medicament carrier cassette for use in a dry powder inhalator device in accordance with the present invention.
Figure 3:
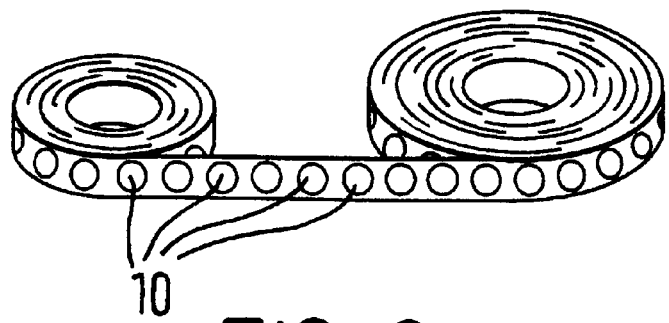
FIG. 3 is a perspective view of a third representative medicament carrier cassette for use in a dry powder inhalator device in accordance with the present invention.
Figure 4A:
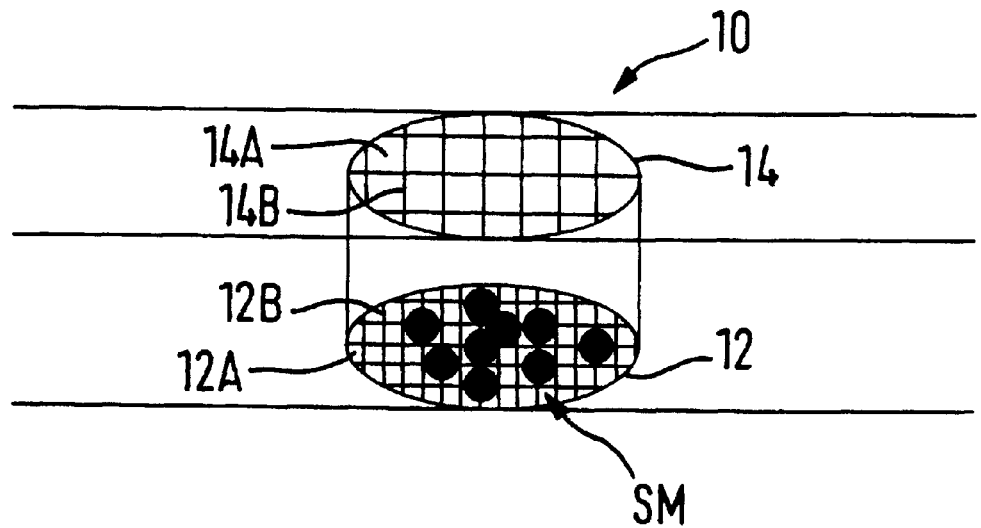
FIG. 4A is a schematic view of an individual medicament carrier with two screens and containing agglomerated medicament powder particles which may be utilized in the representative cassettes shown in FIGS. 1–3.
Figure 4B:
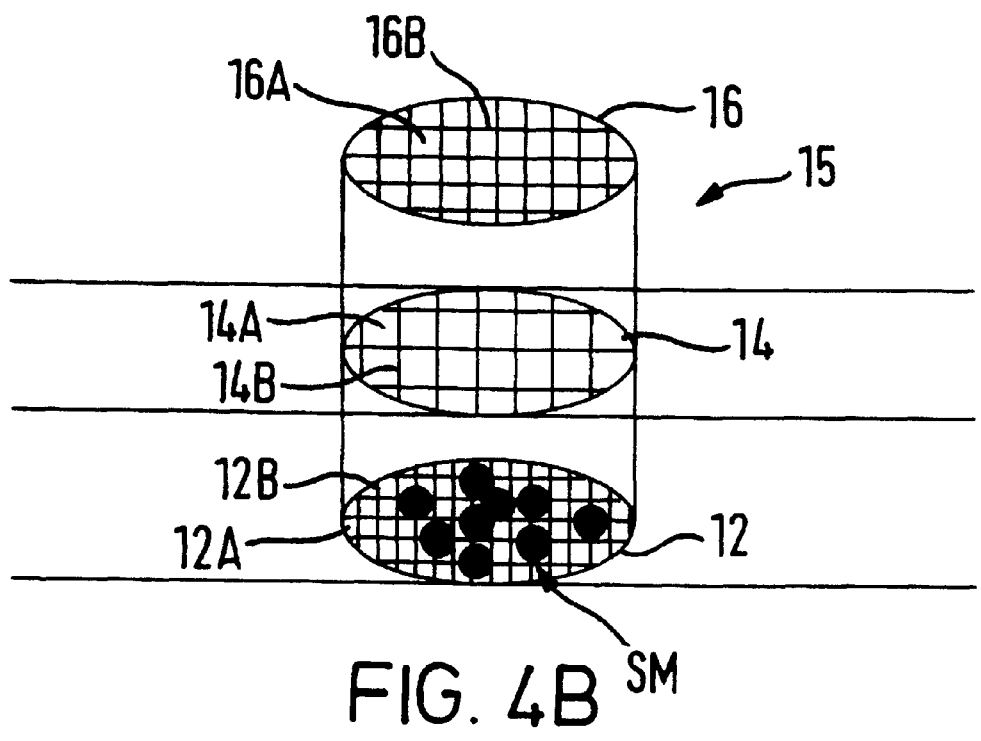
FIG. 4B is the carrier of FIG. 4A but with an optional third screen.

Particularly, as shown in FIGS. 4A, 4B, and 5, interstices 12A should be smaller in width than interstices 14A; however, interstices 12A may be the of the same size or larger in width than interstices 14A. Interstices 12A, 14A may suitably be of a generally square shape, but also may be round, oval, hexagonal, octagonal, diamond, rhomboid, et cetera. Particularly, first screen 12 should be of 400 mesh when SS and of 169 mesh when ETFE, which is a width for each interstice 12A of approximately 38 micrometers and 70 micrometers, respectively, whereas second screen 14 is of 250 mesh SS, which is a width for each interstice 14A of approximately 63 micrometers.

The present invention provides for depositing a prescribed dose of dry powdered agglomerated medicament particles SM (which typically are generally sphere-shaped and thus below are colloquially referred to as "spheronized medicament" particles), substantially on surface 12B of first screen 12 (see FIG. 4) and not primarily within the interstices 12A thereof.

Thus, surface 12B serves as a carrier surface for particles SM. Particles SM suitably have a particle size from about 0.05 millimeter to about 2.0 millimeter, or even more, such as 3.0 millimeter. Particularly, the particle size should be from about 0.1 millimeter to about 1.0 millimeter, more particularly from about 0.2 millimeter to about 0.9 millimeter. The size (from about 0.05 mm to about 3.0 mm) of particles SM is relatively large as compared to prior art micronized particles (typically having a particle size of <0.01 mm, more typically <0.005 mm) used with prior art devices, and thus, the size of particles SM helps them to remain on carrier surface 12B and not become impregnated within interstices 12A.

The respirable powdered medicaments for inhalation therapy or systemic absorption via the respiratory tract to treat respiratory disorders such as asthma, bronchitis, chronic obstructive pulmonary diseases and chest infection may be selected from, but not limited to, the group consisting, for example, analgesics, e.g., codeine, dihydromorphine, ergotamine, fentanyl or morphine; anginal preparations, e.g. diltiazem; antiallergics, e.g. cromoglycate, ketotifen or neodocromil; antiinfectives e.g. cephalosporins, penicillins, stretomycin, sulphonamides, tetracyclines and pentamidine; antihistamines, e.g. methapyrilene; anti-inflammatories, e.g. fluticasone propionate, beclomethasone dipropionate, flunisolide, budesonide or triamcinolone acetonide; antitussives, e.g. noscapine; bronchodilators, e.g. salmeterol, salmbutamol, ephedrine, adrenaline, fenoterol, formoterol, isoprenaline, metaproterenol, phenylephrine, phenylpropanolamine, pirbuterol, reproterol, rimiterol, isoetharine, terbutaline, tulobuterol, orciprenaline, or (−)4-amino-3,5-dichloro-α-[[[6-[2-(2-pyridinyl)ethoxy]hexyl]amino]methyl] benzenemethanol; diuretics, e.g. amiloride; anticholinergics, e.g. ipratropium, atropine, oxitropium; hormones, e.g., cortisone, hydrocortisone or prednisolone; xanthines e.g. aminophylline, choline theophyllinate, lysine theophyllinate or theophylline and therapeutic proteins and peptides, e.g. insulin or glucagon. Additional medicaments include isoproterenol, metaprotarenol, pirbuterol, triacetonide, bambuterol, and mometasone. Further medicaments may be selected from any other suitable drug useful in inhalation therapy. It will be clear to a person skilled in the art that, where appropriate, the medicaments may be used in the form of salts (e.g. as alkali metal or amine salts or as acids addition salts) or as esters (e.g. lower alkyl esters) or as solvates (e.g. hydrates) to optimise the activity and/or stability of the medicament. Preferred medicaments are salbutamol, salmeterol, fluticasone propionate, beclomethasone dipropionate, terbutaline, cromoglycate, budesonide, and triamcinolone acetonide and/or salts thereof.

The medicament may, when deemed advantageous, include a suitable excipient acceptable for inhalation into the human body, which may be selected from organic excipients, such as polysaccharides (i.e., starch, cellulose, and the like), lactose, glucose, mannitol, amino acids, and maltodextrins, or may be inorganic excipients, such as calcium carbonate and sodium chloride. The excipient may be included with the medicament via well known methods, such as by admixing, co-precipitating, and the like.

The size of the dose of particles SM depends upon the drug used. For instance, SH, which is a common drug used for treatment of asthma, is normally dispensed in single doses of about 50 micrograms. Thus, each 50 microgram medicament dose of such a drug is deposited on surface 12B of first screen 12.

As can be seen in FIG. 5, interstices 12A of first screen 12 permit access of an external air flow, air jet, or air pulses or a combination thereof through the exposed area of medicament carrier 10 when carrier 10 is positioned within a suitable dry powder inhalator (not shown) so that particles SM can be entrained in the air which is then inhaled by the patient through an inhalator mouthpiece (not shown) in communication with the air stream, air jet, or air flow in the direction of arrows AF. When powdered agglomerated medicament particles SM are removed by air flow AF entering through interstices 12A of first screen 12 and are entrained and/or disaggregated by air flow AF therethrough, then, first screen 12 serves to present powdered agglomerated medicament particles SM to the path of air flow AF and will act as a source of multiple air jets on powdered agglomerated medicament particles SM. It is noted that air flow AF may be provided to carrier 10 by the patient or by assist devices, such assist devices including, but not limited to, pneumatic, acoustic, electrostatic, mechanical, electromechanical, vibration, or a combination thereof.

More particularly, powdered spheronized medicament particles SM are primarily deposited on surface 12B of first screen 12 and span a significant number of interstices 12A of first screen 12 (see FIG. 4). The number of agglomerated particles SM in physical contact with the screen is significantly reduced. Therefore, the amount of energy required to disaggregate the particles further into the respirable particle size range is minimized (as opposed, for example, to strictly interstitial deposit of the powdered medicament). Also, the agglomerate minimizes the number of particles in physical contact with the screen, and therefore, reduces the probability of having an incomparability between the medicament and the screen.

The thickness of the layer of dry powdered medicament particles SM on surface 12B of first screen 12 can be selected so as to minimize the degree of particle-particle contact. The air pulse, air jet, or air flow AF or combination thereof directed at particles SM will serve to provide initial shear to the dose of powdered medicament and sweep it off of first screen 12, to suck or to blow the dose off of first screen 12 by virtue of the Bernoulli effect, and/or to burst through the dose-bridging interstices 12A. The high shear forces and turbulence experienced by the deposited dry powdered agglomerated medicament particles SM will result in removal of particles SM since each interstice 12A of first screen 12 will act as a nozzle or jet.

After powdered medicament particles SM are removed by the air flow from first screen 12 and entrained in the air flow therethrough, second screen 14 is utilized so as to shear and further to disaggregate drug particles SM due to impaction and high shear forces resulting from contact of agglomerated powdered medicament particles SM with second screen 14 and resulting from air flow velocity gradients experienced by powdered medicament particles SM. More particularly, providing an air stream AF to carrier 10 entrains relatively large powdered medicament particles SM and moves them from first screen 12 through interstices 14A of second screen 14 whereby the particles are sheared by screen 14 into relatively small sheared particles SSP of the desirable respirable particle size range.

As particles SM impact surface 14B of screen 14, become sheared, and pass through interstices 14A, particles SM become small sheared particles SSP and typically acquire a mass median aerodynamic diameter particularly from about 0.5 micrometers to about 6.0 micrometers, more particularly from about 1 micrometers to about 4.5 micrometers, with >50% of the mass of particles SSP, more particularly >70% of the mass of particles SSP, preferably having a mass median aerodynamic diameter <6 micrometers, more preferably <5 micrometers, and then particles SSP pass into the patient's lungs. As noted above vis-a-vis prior art dry powder inhalators, it is particularly useful that particles of respirable particle size range have more than 50% thereof with a mass median aerodynamic diameter <6 micrometers, more particularly <5 micrometers, which is achieved with the present invention.

Various devices and methods are known for use in agglomerating fine particles into larger particles. It is noted that agglomeration typically results in the particles having a generally spherical shape, and hence, agglomeration is often colloquially referred to as "spheronization" and the resultant agglomerated particles referred to as "spheronized medicament" particles SM. These devices include, but are not limited to, vibrators, tumblers (e.g., inclined drums or disks), extruders (e.g., pellet mills and screw extruders), mixers (e.g., pin mixers and spiral path mixers), fluid bed granulators, sprayers, high pressure compactors, and sinterers.

A survey of commercial agglomeration equipment available revealed that the smallest scale commercially available device is suitable for spheronization of 200 g quantities of micron-sized particles. However, as can be seen from the Examples below, it was desired to spheronize quantities of about 20 mg.

Thus, as depicted schematically in FIG. 6, a laboratory scale tumbler/agglomeration apparatus 20, useful in forming spheronized medicament powder particles SM in accordance with the present invention was assembled. A 20 milliliter glass scintillation vial SV was secured to a ROTAVAP™ brand rotator R, and fine particulate medicament M was placed in vial SV for tumbling thereof to form powdered spheronized medicament particles SM as are illustrated in the photographs of FIGS. 7 and 8.

Figure 7:
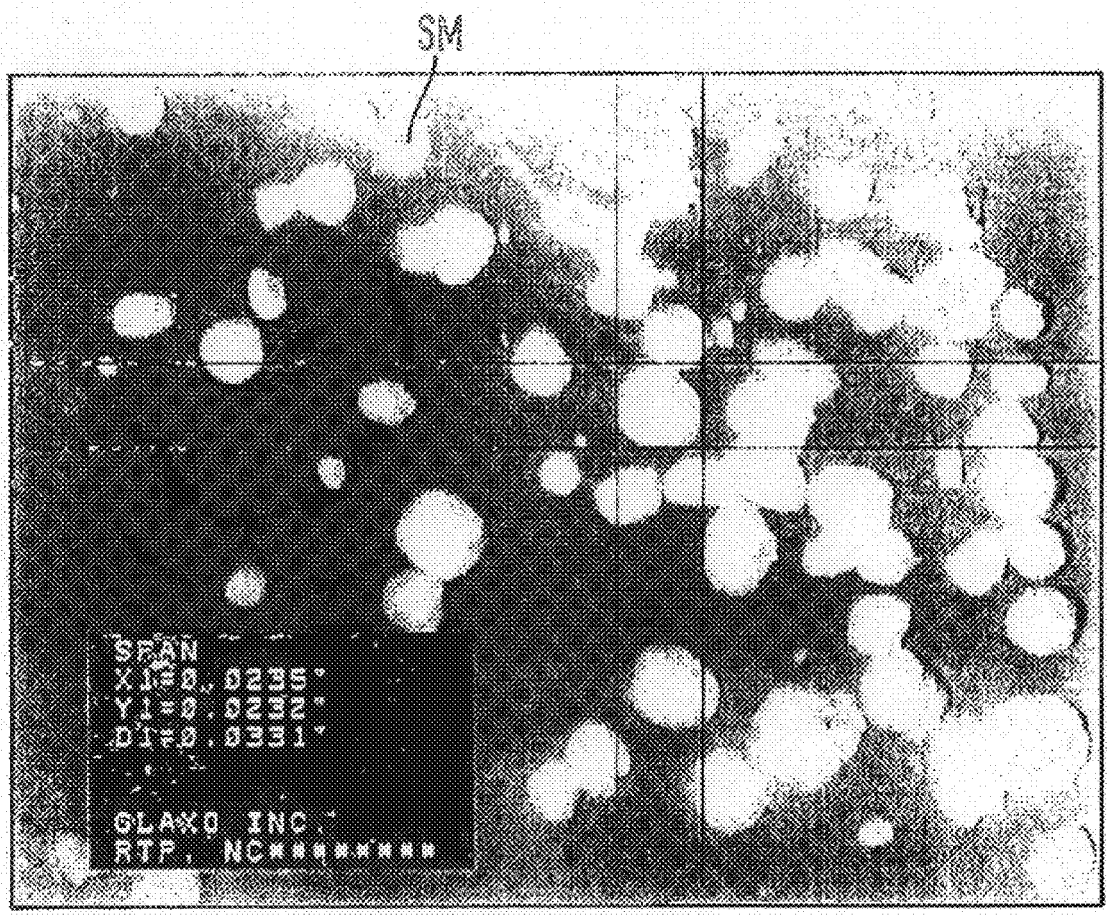
Figure 8:
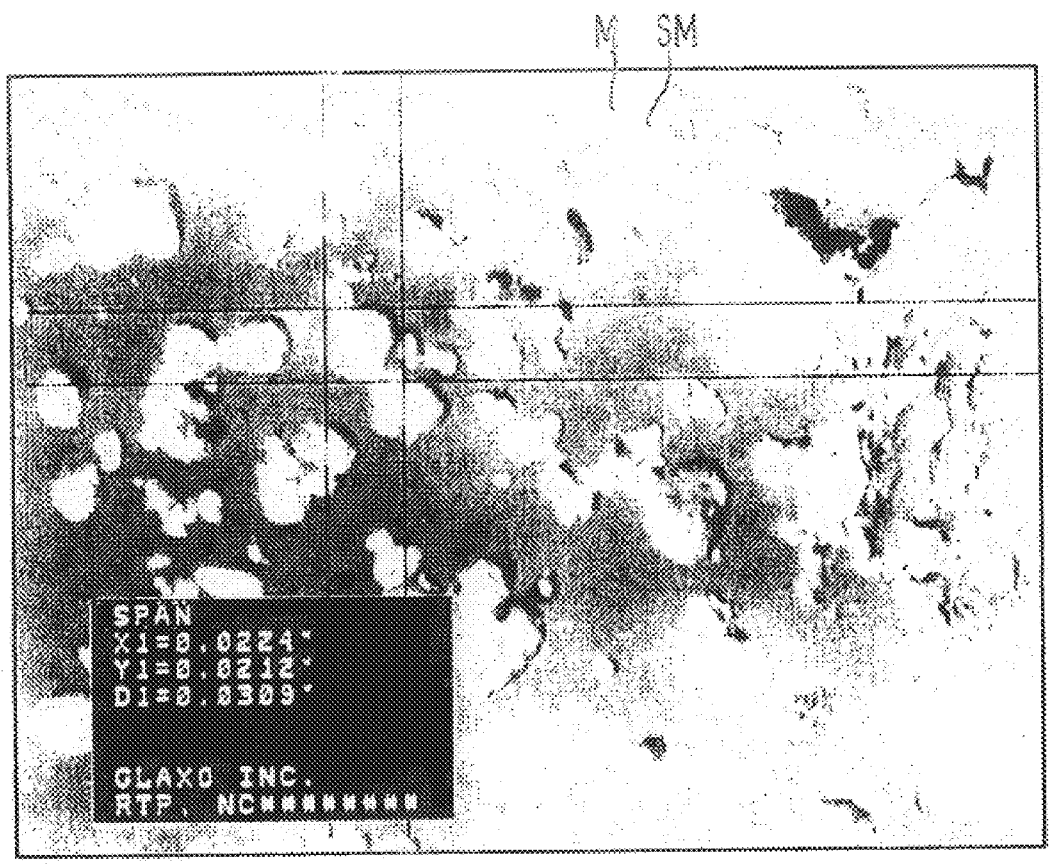

More particularly, FIG. 7 is a photomicrograph of tumble-agglomerated spheronized medicament particles SM of the medicament, beclomethasone dipropionate. FIG. 8 is a photomicrograph of tumble agglomerated. spheronized medicament particles SM of the medicament, salmeterol, and also in the same field of view to demonstrate the difference in particle size, of micronized powder particles M.

The tensile strength of the spheres will vary depending on the particular medicament being agglomerated, the particular agglomeration device and method therefor, and the extent of impaction during the agglomeration (i.e., spheronization) of fine particulate medicament into spheronized medicament particles SM from about 0.05 mm to about 3.0 mm in size. In the event that the agglomerated spheres have a weak enough tensile strength so that a large storage container of them, such as a kilogram quantity, would result in upper spheres crushing lower spheres in the container prior to deposition of the spheres onto carrier screen 12, then spheronization should be accomplished in-line so that the formed spheres can be deposited directly after spheronization onto carrier screen 12 or accomplished in-situ in carrier 10 (between screens 12 and 14).

Hence, with the present invention, medicament particles SM may be applied directly onto carrier screen 12, without the use of any suspending agent. Such suspending agents are unnecessary, although they may be used. In contrast, in the prior art, dry powdered medicament is admixed with a suspending agent, such as dichloromethane, and the resultant suspension applied to the carrier.

LABORATORY EXAMPLES

Example 1

Spheronised, microfine, spray-dried medicament powder of each of the two medicaments, salbutamol sulfate and amiloride HCl (abbreviated herein as Alb S and Amil HCl, respectively), are employed in this example. Non-spheronised spray dried medicament is employed for comparison.

Spheronisation is accomplished through the following procedure. A mass of 20 milligrams of Alb S microfine powder is placed in a 20 milliliter glass scintillation vial (available from Kimble Glass of New Jersey). The vial is attached to a ROTAVAP™ (as depicted in FIG. 6), which can rotate the attached vial from 0 to 20 rotations per minute (rpm).

The vial is rotated for approximately 10 minutes at approximately 40 to 50 rpm. It is noted that the particular 20 milliliter vial has an inner diameter of 24 mm, so that if a different size container is employed, the rpm would need to be adjusted accordingly to maintain the same linear velocity at the inner wall surface of the vial.

The principal axis of the vial downward from the vertical direction is 900 or slightly larger (as depicted in FIG. 6), which is employed so that the powder was evenly distributed along the inside surface of the vial during tumbling.

However, it is noted that angles smaller than 900 will also work. No solvent or binders are employed with the medicament during the tumbling. The tumbling is conducted at ambient conditions (25° C. and about 50% RH) and results in spheres of Alb S.

The tumbling is repeated with Amil HCl in the same manner as described above for Alb S, except that the vial is rotated at approximately 200 rpm, and results in spheres of Amil HCl.

Next, a DISKHALER™ (a medicament dispersing device commercially available from Glaxo Wellcome Inc.) is employed. The 4-blister compartment is removed from the holder portion of the DISKHALER™, and each dosage of the spheres of each Alb S and Amil HCl is loaded onto the bottom of the holder portion of the DISKHALER™, the bottom serving as a carrier surface. The DISKHALER™ has a screen, which serves as a shearing and impaction screen for the spheres.

For the comparisons, each dosage of the spray dried microfine medicaments of each of Alb S and Amil HCl is loaded onto the bottom of the holder portion of the DISKHALER™, the bottom serving as a carrier surface. Then, the screen of the DISKHALER™, serves to direct the air jet, thus helping to entrain the particles in the air jet, as the screen does in the commercially available DISKHALER™.

Next, each DISKHALER™ device with its respective medicament, was attached to an AUTOBREATHER™, (available from API of Hadley, Mass.) for dispersion of the medicament carrier. The AUTOBREATHER™ is a device which simulates inspiration by a human through the mouth at 60 liters/minute, with an acceleration of 19 liters/second$^2$ and a total volume of 1 liter.

The inspired powder (which was approximately 1 milligram) is then drawn into an AEROSIZER™ (available from API of Hadley, Mass.) unit for aerodynamic particle size analysis. The extent to which the powder is dispersed is measured by the mass median aerodynamic diameter (MMAD) in micrometers, and the percentage that is less than 6 micrometers, preferably less than 5 micrometers, is indicative of desirable particle size for inhalation into the lungs. The photomultiplier tubes of the AEROSIZERT™ are operated at 1100 volts, and the data are analyzed in an auto-combine mode with software version 5.02.37 available from API of Hadley, Mass.

The results for the dispersed spray dried particles of medicaments (comparisons) and the dispersed tumble-agglomerated spheres of medicaments are summarized in Table 1 below.

TABLE 1

| Drug | MMAD (micrometers) | % Mass < 5 micrometers | Sample Type |
|---|---|---|---|
| Alb S | 6.64 | 34 | comparison-spray dried, microfine |
| Alb S | 3.5 | 83 | spheres (spray dried) |
| Amil HCl | 6.3 | 39 | comparison-spray dried, microfine |
| Amil HCl | 3.9 | 60 | spheres (spray-dried) |
| — | — | — | — |

As can be seen from Table 1, for the medicament spheres dispersed from the carrier, the resultant small sheared particles have a smaller size and a greater percentage of them are under the desirable inhalation size of <5 micrometers, as compared to the microfine medicament dispersed from the carrier.

Example 2

The tumble-agglomeration procedure with the 20 milliliter glass vial attached to the ROTAVAP™ as described in Example 1 above is repeated for the medicaments beclomethasone dipropionate and salmeterol hydroxynapthoate.

A photomicrograph of the resultant spheres of beclomethasone dipropionate is shown in FIG. 7. From the scale noted on the photomicrograph, it can be seen that the spheres have an average particle diameter size of about 0.033 inch (about 0.84 mm).

A photomicrograph of the resultant spheres of salmeterol hydroxynapthoate is shown in FIG. 8. From the scale noted on the photomicrograph, it can be seen that the spheres have an average particle diameter size of about 0.031 inch (about 0.78 mm). Additionally, for comparison, micronized powder particles are shown in the same field of view in the photomicrograph in FIG. 8 to demonstrate the difference in particle size between spheronized medicament and micronized medicament.

Example 3

The procedure of Example 1 for tumble-agglomeration of a medicament into spheres and then evaluation of the MMAD of the resultant small sheared particles after dispersion of the spheres is repeated with the medicament, fluticasone propionate (abbreviated herein as FP), but with the following changes.

Instead of the AEROBREATHER™ device for simulation of inspiration by a human, employed is a device consisting of the following components: 2.5 liter stainless steel air reservoir (available from WHITEY), pressure transducer (Model PX605 available from OMEGA) with digital readout (Model DP205-E available from OMEGA), air pulse exit valve timer (Part No. CNT-35-96 available from POTTER & BRUMFIELD), 2 miniature solenoid gas valves (12 volts DC, 100 psig, Model No. CP98300-60 available from COLE PARMER, and Model 9-567-90, Series 9 available from GENERAL VALVE), 2 meter valves (available from WHITEY), 5 milliliter GASTIGHT® syringe (available from HAMILTON), clamp to hold and position screen holder assembly, and polytetrafluoroethylene 1/4 inch-28 male T-union used as nozzle (Part No. 13-22-062-2, 0.89 inches long with 0.0625 inch internal diameter available from GENERAL VALVE).

In operation, a metering valve is connected to a regulated air pressure source open to allow air to pass into the 2.5 liter chamber to achieve the desired pressure, typically 84 psig. The first solenoid valve is opened to pressurize the chamber between the 2 solenoid valves, and the volume was controlled by the syringe and the dead volume of the T-union. The timer opens the second solenoid valve for a defined period (which was 100 milliseconds) resulting in a controlled pressure pulse of air through the nozzle.

The first carrier surface is the surface of a first screen instead of the bottom of the holder portion of the DISKHALER™, and thus, the impaction screen is the second screen. The agglomerated FP is loaded in respective 2-screen carriers as depicted in FIG. 4A by transferring approximately 50 micrograms dosage of the spheronized powder with a spatula from the vial into the first screen of the carrier and then placing the second screen thereover.

For all carriers, each screen is of stainless steel. The first screen is of 400 mesh and the second screen is of 250 mesh, and the 2 screens are spaced apart by 0.03 inch (0.76 millimeter). The microgram dose weights of the spheronized FP loaded in each carrier range from 44.4 micrograms to 54.1 micrograms. Six carriers containing the spheronized FP are placed in a screen holder assembly so that each of the carriers could be impacted with the controlled pressure pulse of air from the device described in the two paragraphs above.

More specifically, the screen holder assembly consists of 2 aluminum cover plates (3 inches×2 inches), 2 stainless steel masks (3 inches×1 inch), and 1 polytetrafluoroethylene spacer (3 inches x 718 inch). The stainless steel mask and the spacer contains 6 matching holes for holding the 6 carriers with the 2-screen mode.

The results are as follows for the small sheared particles resulting when the medicament spheres were dispersed from the carrier. The MMAD ranges from 3.2 micrometers to 3.3 micrometers, with an average of 3.2 micrometers. From disaggregation of large spheronized particles into small sheared particles, the percentage of the mass of the particles under 5.8 micrometers is 73.9%.

It will be understood that various details of the invention may be changed without departing from the scope of the invention. Furthermore, the foregoing description is for the purpose of illustration only, and not for the purpose of limitation—the invention being defined by the claims.

What is claimed is:

1. A medicament carrier for use in an inhalator device, said medicament carrier comprising:
   (a) a first screen having a surface defining a plurality of interstices therein; and
   (b) a second screen spaced apart from the first screen, and the second screen having a surface defining a plurality of interstices therein; and
   (c) a dose of medicament, said dose comprising performed, spheronized dry powder agglomerated medicament particles from about 0.05 millimeters to about 3.0 millimeters in size, each of said agglomerated particles comprising individual particles of respirable size, said agglomerated medicated particles being positioned upon, but not being formed upon, said first screen such that said agglomerated medicament particles are located between said first and second screens, and span several of the interstices of the first screen, with the spanned interstices of said first screen remaining substantially open and partially free of the agglomerated particles.

2. The medicament carrier according to claim 1, wherein the first screen is spaced from the second screen from about 0.05 to about 3.0 millimeter.

3. The medicament carrier according to claim 1, wherein each screen is formed from a material selected from the group consisting of woven materials and non-woven materials.

4. The medicament carrier according to claim 3, wherein the woven materials are selected from the group consisting of natural fibers, polymeric synthetic fibers, metal fibers, and ceramic fibers.

5. The medicament carrier according to claim 4, wherein the fibers are surface plasma-treated or metal coated.

6. The medicament carrier according to claim 3, wherein the non-woven materials are selected from the group consisting of punched blanks, stamped blanks, and photoacid etched materials.

7. The medicament carrier according to claim 6, wherein the blanks are metal or the photoacid etched materials are metal.

8. The medicament carrier according to claim 1, wherein the interstices of the first screen and of the second screen are of a shape selected from the group consisting of square, round, oval, hexagonal, octagonal, rhomboid, diamond, and combinations thereof.

9. The medicament carrier according to claim 1, wherein the interstices of the first screen and of the second screen are at least about 10 micrometers in width.

10. The medicament carrier according to claim 1, wherein the interstices of the first screen are of a smaller size than the interstices of the second screen, the interstices of the first screen are of a larger size than the interstices of the second screen, or the interstices of the first screen are of the same size as the interstices of the second screen.

11. The medicament carrier according to claim 10, wherein the interstices and surface of the first screen are of a size such that the first screen is of 400 mesh or of 169 mesh, and the interstices and surface of the second screen are of a size such that the second screen is of 250 mesh.

12. The medicament carrier according to claim 1, wherein the agglomerated medicament particles comprise a medicament selected from the group consisting of albuterol, amiloride, terbutaline, isoproterenol, metaprotaranol, pirbuterol, salmeterol, fluticasone propionate, budesonide, beclomethasone dipropionate, disodium cromoglycate, bambuterol, mometasone, insulin and triacetonide, and pharmaceutically acceptable salts thereof.

13. The medicament carrier according to claim 1, further including a third screen, spaced apart from one of the first screen or the second screen, and the third screen having a surface defining a plurality of interstices therein.

14. The medicament carrier according to claim 1, in combination with an inhalator device.

15. A process for forming a medicament carrier to use in a dry powder inhalator device comprising the steps of:
   (a) providing a quantity of powdered medicament particles of respirable size;
   (b) providing a medicament carrier which includes at least a first screen and a second screen spaced therefrom, each screen having a respective surface defining a plurality of interstices therein, and the first screen serving as an initial disaggregation screen and the second screen serving as a shearing and impaction screen;
   (c) agglomerating said powdered medicament particles of respirable size into performed, spheronized dry powdered medicament agglomerates being larger in size than the interstices of the first screen, said medicament agglomerates being from about 0.05 millimeters to about 3.0 millimeters in size;
   (d) metering a dose of said performed, spheronized dry powdered medicament agglomeratesto form a metered dose of agglomerated particles;
   (e) positioning said metered does of agglomerated particles onto the first screen, and arranging the carrier such that the metered dose of agglomerated particles is positioned between said first and second screens, such that the performed, spheronized dry powdered medicament agglomerates span a number of interstices of said first screen portion and the interstices thereof are at least partially open and free of the preformed, spheronized dry powder agglomerated medicament particles.

16. The process according to claim 15, wherein agglomerating is accomplished with a device selected from the group consisting of a vibrator, tumbler, an extruder, a mixer, a fluid bed granulator, a sprayer, a high pressure compactor, and a sinterer.

17. The process according to claim 15, wherein the first screen is spaced from the second screen from about 0.05 millimeters to about 3.0 millimeters.

18. The process according to claim 15, wherein each screen is formed from a material selected from the group consisting of woven materials and non-woven materials.

19. The process according to claim 18, wherein the woven materials are selected from the group consisting of natural fibers, polymeric synthetic fibers, metal fibers, and ceramic fibers.

20. The process according to claim 19, wherein the fibers are surface plasma-treated or metal coated.

21. The process according to claim 18, wherein the non-woven materials are selected from the group consisting of punched blanks, stamped blanks, and photoacid etched materials.

22. The process according to claim 21, wherein the blanks are metal or the photoacid etched materials are metal.

23. The process according to claim 15, wherein the interstices of the first screen and of the second screen are of a shape selected from the group consisting of square, round, oval, hexagonal, octagonal, rhomboid, diamond and combinations thereof.

24. The process according to claim 15, wherein the interstices of the first screen and of the second screen are at least about 10 micrometers in width.

25. The process according to claim 15, wherein the interstices of the first screen are of a smaller size than the interstices of the second screen, the interstices of the first screen are of a larger size than the interstices of the second screen, or the interstices of the first screen are of the same size as the interstices of the second screen.

26. The process according to claim 25, wherein the interstices and surface of the first screen are of a size such that the first screen is of 400 mesh or of 169 mesh, and the interstices and surface of the second screen are of a size such that the second screen is of 250 mesh.

27. The process according to claim 15, wherein the agglomerated medicament particles positioned onto the first screen are selected from the group consisting of albuterol, amiloride, terbutaline, isoproterenol, metaprotaranol, pirbuterol, salmeterol, fluticasone propionate, budesonide, beclomethasone dipropionate, disodium cromoglycate, bambuterol, mometasone, insulin, and triacetonide, and pharmaceutically acceptable salts thereof.

28. The process according to claim 15, wherein positioning the agglomerated powdered medicament particles onto the first screen is accomplished free of a suspending agent.

29. The process according to claim 15, further including the steps of (a) providing a third screen having a surface defining a plurality of interstices therein and (b) positioning said third screen spaced part from one of the first screen or the second screen, such that an air flow path is created between the interstices of the first, second and third screens.

30. A process for dispersing powdered medicament from a medicament carrier adapted for use in a dry powder inhalator device, said medicament carrier including at least a first screen and a second screen therefrom, each screen having a respective surface defining a plurality of interstices therebetween, and at least one dose of preformed spheronized dry powdered agglomerated medicament particles comprising agglomerated particles from about 0.05 to about 3.0 millimeters in size positioned between the first carrier screen and the second carrier screen such that the first screen serves as a carrier screen for the preformed spheronized dry powdered agglomerated medicament particles and the interstices thereof are at least partially open and free of the agglomerated medicament particles, and the second screen serves as a shearing screen for the preformed spheronized dry powdered agglomerated medicament particles, said process comprising:

(a) providing an air flow to the carrier to entrain and cause initial disaggregation of the preformed spheronized dry powdered agglomerated medicament particles, the first screen serving to present the preformed spheronized dry powdered aggolmerated medicament particles to air flow and serving as a source of air particles, and to impact them on the surface of the second screen, whereby the preformed spheronized dry powdered agglomerated medicament particles are sheared and further disaggregated by the surface of the second screen into smaller powder particles of respirable particle size that move through the interstices of the second screen.

31. The process of claim 30, wherein the particles of respirable particle size range have a mass median aerodynamic diameter from about 0.5 micrometers to about 6.0 micrometers.

32. The process of claim 31, wherein the particles of respirable particle size range have more than 50% thereof with a mass median aerodynamic diameter <6 micrometers.

33. The carrier according to claim 1, wherein the preformed spheronized dry powdered medicament agglomerates are agglomerated without the use of binders or a solvent.

34. The process according to claim 15, herein the preformed spheronized dry powdered medicament agglomerates are agglomerated without the use of binders or a solvent.

35. The process according to claim 30, wherein the preformed spheronized dry powdered medicament agglomerates are agglomerated without the use of binders or a solvent.

* * * * *